(12) United States Patent
Koizumi et al.

(10) Patent No.: US 6,879,393 B2
(45) Date of Patent: Apr. 12, 2005

(54) DEFECT INSPECTION APPARATUS FOR PHASE SHIFT MASK

(75) Inventors: Yasuhiro Koizumi, Tokyo (JP); Shiaki Murai, Tokyo (JP); Shigeru Noguchi, Tokyo (JP); Katsuhide Tsuchiya, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 09/920,450

(22) Filed: Aug. 1, 2001

(65) Prior Publication Data

US 2002/0036772 A1 Mar. 28, 2002

(30) Foreign Application Priority Data

Aug. 3, 2000 (JP) ........................................ 2000-235796

(51) Int. Cl.[7] ............................................... G01N 21/00
(52) U.S. Cl. ................................. 356/237.5; 356/237.4
(58) Field of Search ............................ 356/237.4, 237.5

(56) References Cited

U.S. PATENT DOCUMENTS 5,220,403 A * 6/1993 Batchelder et al. ......... 356/450
5,764,363 A * 6/1998 Ooki et al. .................. 356/364
6,018,392 A * 1/2000 Tzu et al. .................... 356/511
6,064,477 A * 5/2000 Matsumoto et al. ...... 356/237.2
6,078,386 A * 6/2000 Tsai et al. ................. 356/237.1

* cited by examiner

Primary Examiner—Michael P. Stafira
Assistant Examiner—Juan D Valentin II
(74) Attorney, Agent, or Firm—Dellett & Walters

(57) ABSTRACT

The present invention relates to a defect inspection apparatus for a phase shift mask that is capable of detecting phase shifter defects that cannot be detected by conventional inspection techniques, by a simple method using an optical method and a comparison of electric signals. In a defect inspection apparatus for a phase shift mask having a phase shifter pattern provided on a mask transparent substrate 1, after the phase shifter pattern has been formed, a phase shifter defect inspection is performed from the mask transparent substrate 1 side of the phase shift mask 1. To perform the defect inspection, light 12 is applied to the phase shift mask 1 from the mask transparent substrate 1 side thereof, and reflection images of at least two different phase shifter pattern fabricated regions are captured by photoelectric conversion light-receiving elements 15a and 15b. The respective image signals 17 and 18 of the reflection images are compared with each other to detect a defect on the mask from the difference between the signals.

6 Claims, 2 Drawing Sheets

DEFECT INSPECTION APPARATUS FOR PHASE SHIFT MASK

BACKGROUND OF THE INVENTION

The present invention relates to a defect inspection apparatus for a phase shift mask. More particularly, the present invention relates to a defect inspection apparatus for detecting phase shifter defects on a phase shift mask.

With the achievement of miniaturization of semiconductor integrated circuits, circuit elements and wiring patterns have become small and fine to such an extent that the design rule therefor are of the order of submicrons. Under these circumstances, a reduction in the pattern transfer accuracy is a serious problem in a photolithography process wherein an integrated circuit pattern on a photomask is transferred onto a semiconductor wafer by light of i-line (wavelength 365 nm), KrF-line (wavelength 245 nm), etc. Accordingly, a photolithography process requiring a particularly high resolution uses a phase shift (photo) mask in which phase shifters are provided at light-transmitting portions.

The principal structure of phase shift masks is a substrate engraving type phase shift mask produced by engraving a glass substrate to form phase shifters over light-transmitting portions of the mask. A sectional view of such a substrate engraving type phase shift mask is shown in FIG. 2. On a glass transparent substrate 31, a light-shielding pattern 32 of chromium is provided in the form of a repeated pattern, and the transparent substrate 31 is etched at alternate space regions between the adjacent portions of the light-shielding pattern 32 to a depth corresponding to a half of the working wavelength (about 180° in terms of phase difference) to form trenches 33.

Phase shifter defects on such phase shift photomasks may be generated in the mask making process. Examples of phase shifter defects are a partially unfinished phase shifter due to adhesion of a contamination to a region where a 180° phase shifter is to be formed, and an excess or overetched phase shifter due to a resist pinhole or the like present in a region where no phase shifter should be formed.

The edges of phase shifter forming regions are formed under the chromium pattern, and the phase shifter is formed at a light-transmitting portion. For these reasons, all the above-described phase shifter defects cannot be detected by a conventional inspection method using transmitted light or a conventional inspection method in which both the front and back surfaces of a phase shift photomask are illuminated with light and the reflected light and the transmitted light are compared with each other. Therefore, the following inspection method is presently employed. The pattern of a photomask under inspection is transferred onto a wafer by an exposure system, and whether or not there is a defect is checked by an inspection machine using the transferred pattern.

However, in the case of a semiconductor integrated circuit device having a line width of 0.1 µm or less, the pattern defect detection size on the wafer is 10 to 30 nm. Therefore, pattern defects cannot be detected with a wafer defect inspection apparatus.

Under the above-described circumstances, it has become necessary to develop an inspection apparatus for detecting phase shifter defects on a substrate engraving type phase shift mask.

The conventional techniques and problems associated therewith are as follows:

1) Because phase shifters are formed at light-transmitting portions of a mask, it is impossible to detect a phase difference-deviating step defect formed on the glass at a light-transmitting portion by using transmitted light inspecting type inspection apparatus commercially available from KLA-Tencor, Lasertech, etc.
2) Regarding the defect inspection of a substrate engraving type phase shift mask in particular, because the edges of phase shifter forming regions is formed under the chromium pattern, phase shifter defects cannot be detected even by an inspection method in which comparison is made between a transmitted light image from the back surface of the mask and a reflected light image from the front surface of the mask at an arbitrary region in an inspected portion of the mask, e.g. the STARlight (trade name: KLA-Tencor) inspection method, which is another inspection method usable by mask inspection apparatus.
3) With inspection apparatus using reflected light from the front surface where the mask pattern is formed, e.g. 9MD83SR, available from Lasertech, it is impossible to detect defects in a case where the amount of phase difference is small, i.e. 120° or less.
4) As has been stated above, the mask inspection apparatus commercially available at present cannot satisfactorily detect phase shifter defects. For this reason, the conventional practice is to employ the following method to check whether or not there is a defect in a phase shift mask. That is, the pattern of a photomask under inspection is transferred onto a wafer by a wafer exposure system, and the presence of a defect in the phase shift mask is judged by a 2-chip comparing inspection apparatus using the transferred pattern. Accordingly, evaluation cannot be conducted in the mask making process. The wafer process is requested to perform evaluation, resulting in an increase in the number of man-hours needed to carry out the mask making process.
5) Moreover, when circuit patterns become finer, i.e. 0.1 µm or less in line width, in the future with the achievement of further miniaturization, the size of a defect is 10 to 30 nm when such a fine pattern is transferred onto a wafer to evaluate the phase shift mask. The detection sensitivity of the present wafer defect inspection apparatus is not sufficient to inspect the phase shift mask for such small defects. Accordingly, there will be no means for evaluating phase shift masks.

SUMMARY OF THE INVENTION

The present invention was made in view of the above-described circumstances of the prior art. An object of the present invention is to provide a defect inspection apparatus for a phase shift mask that is capable of detecting phase shifter defects that cannot be detected by the conventional inspection techniques, by a simple method using an optical method and a comparison of electric signals.

To attain the above-described object, the present invention provides a defect inspection apparatus for a phase shift mask having a phase shifter pattern provided on a mask transparent substrate. In the defect inspection apparatus, after the phase shifter pattern has been formed, a phase shifter defect inspection is performed from the mask transparent substrate side of the phase shift mask.

In this case, it is desirable to perform the defect inspection in such a manner that light is applied to the phase shift mask from the mask transparent substrate side thereof, and reflection images of at least two different phase shifter pattern fabricated regions are captured. Then, the respective image signals of the reflection images are compared with each other to detect a defect on the mask from the difference between the signals.

The at least two different phase shifter pattern fabricated regions may be phase shifter pattern fabricated regions of chips different from each other.

In this case, it is desirable to capture the reflection images of the at least two different phase shifter pattern fabricated regions through respective magnifying optical systems.

Further, the at least two different phase shifter pattern fabricated regions may be phase shifter pattern fabricated regions in the identical chip pattern.

In this case, it is desirable to capture the reflection images of the at least two different phase shifter pattern fabricated regions through the identical magnifying optical system.

Further, the reflection images obtained by reflected light are, preferably, dark field images obtained by dark field illumination but may be bright field images obtained by bright field illumination.

In the present invention, a phase shifter defect inspection is performed from the mask transparent substrate side of the phase shift mask after the phase shifter pattern has been formed. Therefore, it is possible to check easily the edge configuration of phase shifter pattern fabricated regions, the presence of a phase shifter, the height difference between phase shifters, etc. Accordingly, phase shifter defects can be detected easily.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

The basic principle of the present invention is as follows. To detect a phase shifter defect at phase shifter pattern fabricated regions of a glass substrate of a phase shift mask, light is applied to the mask from the back thereof, and the reflected light from the mask is taken in through a magnifying optical system in such a manner that the phase shifter configuration is magnified. The electric signals of at least two images captured in this way are compared with each other. A coordinates position on the mask where a signal difference is produced is judged to be a phase shifter defective region. The present invention is an inspection system in which light is applied to the back surface of the mask, i.e. the glass substrate side thereof, and a phase shifter inspection is performed by using the reflected light from the back surface of the mask.

An embodiment of the phase shift mask defect inspection apparatus according to the present invention will be described below with reference to FIG. 1.

A phase shift photomask (reticle) 1 in this embodiment is used, for example, at an exposure step in the process of manufacturing semiconductor integrated circuit devices to transfer a predetermined integrated circuit pattern onto a semiconductor wafer. The photomask 1 has an original integrated circuit pattern formed thereon, which is, for example, 4 or 5 times as large as the actual size of the integrated circuit pattern. The phase shift photomask 1 shown in FIG. 1 is a substrate engraving type phase shift mask similar to that shown in FIG. 2. The phase shift photomask 1 has a light-shielding pattern 2 of chromium provided in the form of a repeated pattern on a glass transparent substrate 7. The transparent substrate 7 has trenches 3 formed by etching the substrate 7 at alternate space regions between the adjacent portions of the light-shielding pattern 2 to a depth corresponding to a half of the exposure wavelength (a phase difference of 180°). A plurality of identical chip patterns are arranged on the same glass substrate 7 at predetermined spaces.

Figure 1:
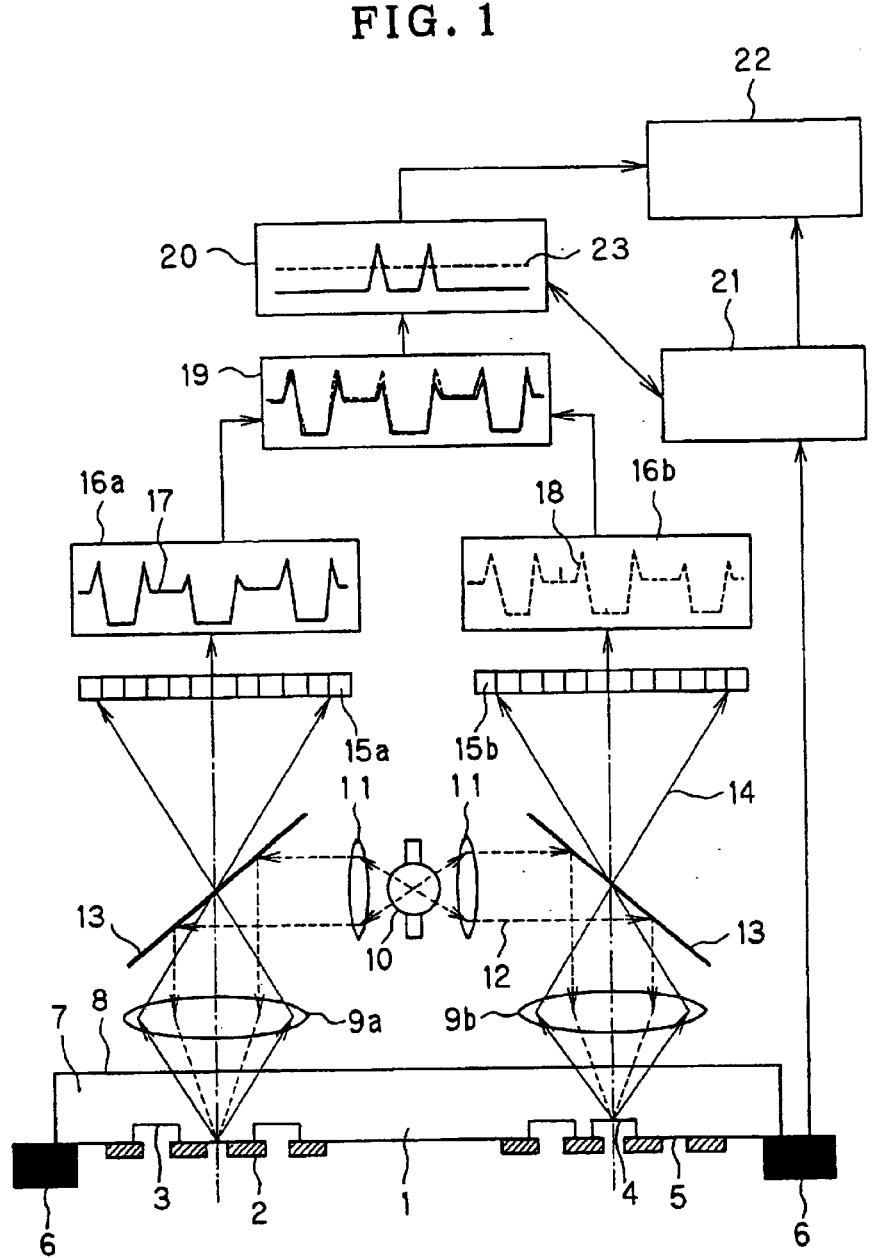
FIG. 1 is a diagram showing the arrangement of an embodiment of the phase shift mask defect inspection apparatus according to the present invention.
Figure 2:
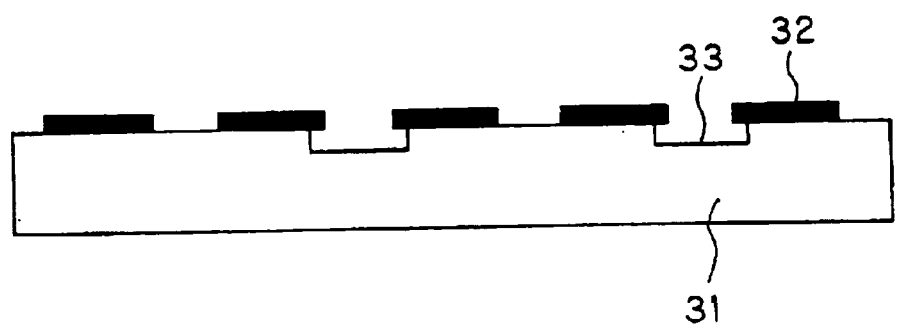
FIG. 2 is a sectional view of a substrate engraving type phase shift mask.

FIG. 1 is a diagram showing the arrangement of a phase shift mask defect inspection apparatus according to an embodiment of the present invention. The defect inspection apparatus has a stage 6 for placing a phase shift photomask 1 to be inspected in such a manner that the back surface of the phase shift photomask 1 faces upward. A light source 10 is provided to apply illuminating light to two regions of different chip patterns on a mask back surface 8 of the glass substrate 7 of the phase shift photomask 1 placed on the stage 6. The defect inspection apparatus further has a pair of image pickup systems having the same characteristics and arranged across the light source 10 from each other. The image pickup systems respectively include objective lenses 9a and 9b and photoelectric conversion light-receiving elements 15a and 15b, e.g. CCDs, positioned in the respective image planes of the objective lenses 9a and 9b.

Beams of illuminating light 12 emitted from the light source 10 in opposite directions to each other pass through respective condenser lenses 11 and are deflected by half-mirrors 13 respectively positioned between the objective lenses 9a and 9b and the photoelectric conversion light-receiving elements 15a and 15b of the two image pickup systems. The deflected beams pass through the objective lenses 9a and 9b, respectively, to illuminate a normal phase shifter forming region 3 of one chip pattern on the phase shift photomask 1 and a phase shifter defective region of another chip pattern, e.g. a defective region 4 containing an excessively formed phase shifter, or a defective region 5 in which a phase shifter is missing. Rays of reflected light 14 from the illuminated regions are taken into the respective image pickup systems through the objective lenses 9a and 9b to form enlarged images of the illuminated regions on the photoelectric conversion light-receiving elements 15a and 15b.

Electric signals obtained by the photoelectric conversion light-receiving elements 15a and 15b are amplified in electric amplifier circuits 16a and 16b connected to the photoelectric conversion light-receiving elements 15a and 15b to output, for example, an electric signal 17 indicating the phase shifter normal region 3 and an electric signal 18 indicating the phase shifter defective region 4 or 5. The two signals 17 and 18 are input to a relational operation circuit 19 where they are processed and then sent to a difference judging circuit 20 for judging the difference between the signals 17 and 18.

When there is a phase shifter defect, a difference is produced between the signals 17 and 18. When the level of the difference exceeds a predetermined threshold value 23, it is judged that there is a defect.

At this time, data concerning the coordinates of the stage 6 measured by a coordinate position measuring circuit 21 is captured. The defect coordinate data is stored in an inspection data storing circuit 22.

The defect inspection is performed for the whole mask surface by scanning the stage 6. After the completion of the inspection, the defect coordinate data is read out from the inspection data storing circuit 22, and the mask 1 is moved to the position where the defect was detected. Then, a judgment is made which of the left and right chip patterns contains the defect by checking the signals 17 and 18 obtained from the left and right image pickup systems at the inspecting position. Data newly obtained by the judgment is stored in the inspection data storing circuit 22.

Thus, the present invention is a mask inspection system wherein light is applied from the back of a Revenson type phase shift mask of the underlying shifter type, e.g. a substrate engraving type phase shift mask. When light is applied from the back of the mask, it is easy to check the edge configuration of phase shifter pattern fabricated regions, the presence of a phase shifter, the height difference between phase shifters, etc. In particular, it is easy to detect a dark field image obtained by dark field illumination. Needless to say, the image used for inspection may be a bright field image obtained by bright field illumination such as that shown in FIG. 1.

Although the present invention has been described above specifically on the basis of an embodiment, it is a matter of course that the present invention is not necessarily limited to the above-described embodiment, and various changes and modifications may be imparted thereto without departing from the gist of the present invention.

For example, if the light source 10 for rear illumination uses a short-wavelength laser beam, e.g. i-line or KrF-line, the detection sensitivity is improved. The two objective lenses may be replaced by a single objective lens system. That is, two or more illuminating light beams are passed through a single object lens to make a comparison between adjacent patterns. With this arrangement, it is also possible to inspect a mask on which single-chip patterns are arranged.

The inspection apparatus according to the present invention is also applicable to the pattern inspection of an engraved panel formed on a large glass substrate for display, for example, besides phase shift masks.

With the achievement of miniaturization of semiconductor devices, a phase shift mask is used as a photomask at a manufacturing step requiring fine processing in the process of manufacturing semiconductor devices.

The phase shift mask gives a phase difference of 180° between light passing through light-transmitting portions arranged across a light-shielding zone from each other in accordance with the exposure wavelength to improve the wafer transfer resolution of the fine light-shielding zone. There is a strict requirement for the accuracy of the phase difference produced at a region where a phase shifter is formed. That is, it is necessary to meet tolerances of ±3°, for example.

For the reasons stated above, it is necessary to detect all defects such as an excess phase shifter and a deficient phase shifter at a phase shifter forming region, and a deviation of the phase difference produced by a phase shifter because these defects cause a resolution failure on the wafer.

The phase shift mask defect inspection apparatus according to the present invention is capable of detecting such phase shifter defects. Therefore, the use of a phase shift mask inspected by this apparatus eliminates a resolution failure on the wafer. In addition, it becomes unnecessary to perform the conventional wafer transfer evaluation.

From the overall viewpoint of products, the present invention is effective for the improvement in accuracy of the design evaluation of high-tech semiconductor devices to which phase shift masks are applied (e.g. SRAMs, DRAMs, microprocessors, and logic elements) and also effective in shortening the period of time required to develop such semiconductor devices. The present invention is also effective in increasing the yield in the mass-production of the semiconductor devices.

What we claim is:

1. A defect inspection apparatus for a phase shift mask having a phase shifter pattern provided on a mask transparent substrate, comprising a lens means for directing light toward at least two different phase shifter pattern fabricated regions of the phase shift mask from a mask transparent substrate side of said phase shift mask which is opposite to a side thereof where said phase shifter pattern has been formed, at least two light receiving elements for receiving light reflected from the at least two different phase shifter pattern fabricated regions of the phase shift mask, wherein the reflection images of said at least two different phase shifter pattern fabricated regions are captured through respective magnifying optical systems, and a difference judging circuit for judging a difference between the light reflected from one of the at least two different phase shifter pattern fabricated regions and another of the at least two different phase shifter pattern fabricated regions.

2. A defect inspection apparatus for a phase shift mask according to claim 1, wherein said at least two different phase shifter pattern fabricated regions are phase shifter pattern fabricated regions of chips different from each other.

3. A defect inspection apparatus for a phase shift mask according to claim 1, wherein said at least two different phase shifter pattern fabricated regions are phase shifter pattern fabricated regions in an identical chip pattern.

4. A defect inspection apparatus according to claim 1 further comprising a stage upon which the phase mask moves, a coordinate positioning measuring circuit for measuring the position of the stage when light is received by said light receiving elements, an inspection data storing circuit for receiving data from said difference judging circuit and for receiving data from said coordinate positioning measuring circuit for determining where a difference has been judged.

5. A defect inspection apparatus according to claim 1 wherein the reflected light is dark field images obtained by dark field illumination or bright field images obtained by bright field illumination.

6. A method of inspecting a phase shift mask, comprising the steps of:

positioning a single piece of phase shift mask below two spaced apart magnifying optical retrieval means;

reflecting light from a light source toward two different regions on the phase shift mask;

receiving light reflected from the two different regions by receiving elements via the two spaced apart magnifying optical retrieval means;

comparing electrical signals from the receiving elements; and judging if any difference detected in said comparing step is greater than a threshold value.

* * * * *